US009089626B2

(12) United States Patent
Bleyer et al.

(10) Patent No.: US 9,089,626 B2
(45) Date of Patent: Jul. 28, 2015

(54) RADIOPAQUE IMPLANTABLE COLLAGENOUS BIOMATERIAL DEVICE

(75) Inventors: Mark W. Bleyer, West Lafayette, IN (US); Michael C. Hiles, West Lafayette, IN (US); Umesh H. Patel, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 169 days.

(21) Appl. No.: 12/762,796

(22) Filed: Apr. 19, 2010

(65) Prior Publication Data

US 2010/0204782 A1 Aug. 12, 2010

(51) Int. Cl.
| | |
|---|---|
| *A61K 9/06* | (2006.01) |
| *A01N 59/00* | (2006.01) |
| *A61F 2/06* | (2013.01) |
| *A61L 27/36* | (2006.01) |
| *A61K 35/38* | (2015.01) |
| *A61L 27/24* | (2006.01) |
| *A61L 27/50* | (2006.01) |
| *A61L 29/00* | (2006.01) |
| *A61L 31/00* | (2006.01) |
| *A61B 19/00* | (2006.01) |

(52) U.S. Cl.
CPC ............. *A61L 27/3683* (2013.01); *A61K 35/38* (2013.01); *A61L 27/24* (2013.01); *A61L 27/3604* (2013.01); *A61L 27/50* (2013.01); *A61L 29/005* (2013.01); *A61L 31/005* (2013.01); *A61B 19/54* (2013.01)

(58) Field of Classification Search
USPC ........ 424/600, 422, 551; 623/1.34, 1.15, 1.47
See application file for complete search history.

(56) References Cited

U.S. PATENT DOCUMENTS

| | | | |
|---|---|---|---|
| 2,172,903 A | 9/1939 | Charping | |
| 3,336,918 A | 8/1967 | Jeckel | |
| 3,562,820 A | 2/1971 | Bernhard | |
| 4,629,458 A * | 12/1986 | Pinchuk .................... 623/1.47 | |
| 4,795,741 A | 1/1989 | Leshchiner et al. | |
| 4,902,508 A | 2/1990 | Badylak et al. | |
| 4,956,178 A | 9/1990 | Badylak et al. | |
| 5,139,505 A | 8/1992 | Palmieri | |
| 5,141,747 A | 8/1992 | Scholz | |
| 5,275,826 A | 1/1994 | Badylak et al. | |
| 5,281,422 A | 1/1994 | Badylak et al. | |
| 5,298,222 A | 3/1994 | O'Leary | |
| 5,372,821 A | 12/1994 | Badylak et al. | |
| 5,460,962 A | 10/1995 | Kemp | |
| 5,554,389 A | 9/1996 | Badylak et al. | |
| 5,601,602 A | 2/1997 | Fowler | |
| 5,609,629 A | 3/1997 | Fearnot et al. | |
| 5,676,146 A | 10/1997 | Scarborough | |
| 5,676,689 A | 10/1997 | Kensey et al. | |
| 5,690,671 A * | 11/1997 | McGurk et al. ............... 606/200 |
| 5,718,012 A * | 2/1998 | Cavallaro ..................... 8/94.11 |
| 5,749,894 A | 5/1998 | Engelson | |
| 5,788,625 A | 8/1998 | Plouhar et al. | |
| 5,885,619 A | 3/1999 | Patel et al. | |
| 5,942,496 A | 8/1999 | Bonadio et al. | |
| 5,997,575 A | 12/1999 | Whitson et al. | |
| 5,997,895 A | 12/1999 | Tarotam et al. | |
| 6,004,269 A * | 12/1999 | Crowley et al. ............... 600/439 |
| 6,024,735 A | 2/2000 | Wolfinbarger | |
| 6,042,605 A | 3/2000 | Martin et al. | |
| 6,048,362 A | 4/2000 | Berg | |
| 6,096,070 A | 8/2000 | Ragheb et al. | |
| 6,099,567 A | 8/2000 | Badylak et al. | |
| 6,206,931 B1 * | 3/2001 | Cook et al. .................. 623/23.75 |
| 6,231,590 B1 * | 5/2001 | Slaikeu et al. ............... 606/200 |
| 6,358,284 B1 | 3/2002 | Fearnot | |
| 6,444,229 B2 | 9/2002 | Voytik-Harbin et al. | |
| 6,475,232 B1 | 11/2002 | Babbs et al. | |
| 6,774,278 B1 | 8/2004 | Rabheb et al. | |
| 2002/0099448 A1 | 7/2002 | Hiles et al. | |
| 2004/0078076 A1 | 4/2004 | Badylak et al. | |
| 2004/0111149 A1 | 6/2004 | Stinson | |

FOREIGN PATENT DOCUMENTS

| | | |
|---|---|---|
| WO | WO 94/26175 | 11/1994 |
| WO | WO 95/22611 | 8/1995 |
| WO | WO 96/24661 | 8/1996 |
| WO | WO 96/25179 | 8/1996 |
| WO | WO 96/31157 | 10/1996 |
| WO | WO 96/31225 | 10/1996 |
| WO | WO 96/32146 | 10/1996 |
| WO | WO 97/19643 | 6/1997 |
| WO | WO 98/22158 | 5/1998 |
| WO | WO 98/25545 | 6/1998 |
| WO | WO 98/25636 | 6/1998 |
| WO | WO 98/25637 | 6/1998 |
| WO | WO 98/26291 | 6/1998 |
| WO | WO 99/44538 | 9/1999 |

OTHER PUBLICATIONS

American National Standard, ANSI/AAMI 10993-1:1994. "Biological Evaluation of Medical Devices—Part 1: Guidance on Selection of Tests". Association for the Advancement of Medical Instrumentation. pp. 9-17.

Baldry, M.G.C., et al., "Disinfection with Peroxygen", Industrail Biocides, 1988, pp. 91-116, K. Payne editor. John Wiley and Sons, Inc. New York.

Block, S. "Peroxygen Compounds", Disinfection, Sterilization and Preservation, 5th Edition 2001. pp. 185-204. Lippincott Williams & Wilkins, Philadephia, PA.

(Continued)

*Primary Examiner* — Maria Leavitt

(74) *Attorney, Agent, or Firm* — Woodard, Emhardt, Moriarty, McNett & Henry LLP

(57) ABSTRACT

Disclosed is a medical device (5) and more particularly, an implantable biomaterial. The biomaterial comprises a radiopaque (22) collagenous biomaterial (10).

11 Claims, 3 Drawing Sheets

(56) References Cited

OTHER PUBLICATIONS

Burgers, "Nerve Growth Factor, Nerve Grafts and Amniotic Membrane Grafts Restore Erectile Function in Rats," J. of Urology, vol. 146:463-468, 1991.

Denton, F.W., "Chlorhexidine", Disinfection, Sterilization and Preservation, S. Block, editor, 5th Edition 2001. pp. 321-336. Lippincott Williams & Wilkins, Philadephia, PA.

Falb R et al., "Characteristics of heparinized surface," Advances in Chemistry Series, 1968, 87:181-5.

Hawley's Condensed Chemical Dictionary, Eleventh Edition, Van Nostrand Reinhold Company, (1987), pp. 886 and 890.

Hodde, J.P. et al., "Gycosaminoglycan Content of Small Intestinal Submucosa: A Bioscaffold for Tissue Repladement" Tissue Engineering, vol. 2, No. 3, 1996, pp. 209-217 XP002063373.

Horak, D. et al., "Hydrogels in Endovascular Embolization, III, Radiopaque Spherical Particles, Their Preparation and Properties", Biomaterials, Mar. 1987, vol. 2, No. 8, pp. 142-145, Butterworth-Heinemann in Association with the Biological Engineering Society, England.

Kawaguchi, "De novo adipogenesis in mice at the site of injection of basement membrane and basic fibroblast grouth factor," Proc. Natl. Acad. Sci., vol. 95, pp. 1062-1066, 1998.

Kocken, "Observations on Initial Cell Loss after Intraportal Hepatocyte Transplantation of 5'-Bromo-deoxy-Uridine-labeled Hepatocytes," Eur Surg Res, 29:411-420, 1997.

Kropp, B.P., "Small-intestinal submucosa for bladder augmentation: a review of preclinical studies," World J. Urol. 1998; 16:262-7.

Kropp, B.P., et al. "Experimental Assessment of Small Intestinal Submucosa as a Bladder Wall Substitute". Urology. Sep. 1995. vol. 46, No. 3. pp. 396-400.

Larsson, R.L. et al., "The stabiilty of glutardialdehyde-stabilized 35-heparinized surfaces in contact with blood," Thromb Haemost. 1977; 37:262-73.

* cited by examiner

RADIOPAQUE IMPLANTABLE COLLAGENOUS BIOMATERIAL DEVICE

CROSS-REFERENCE TO RELATED APPLICATIONS

This application is a continuation of U.S. patent application Ser. No. 10/025,282 filed Dec. 19, 2001, now U.S. Patent No. 7,713,552, which is a continuation of U.S. patent application Ser. No. 09/444,881, filed Nov. 22, 1999, which claims the benefit of U.S. Provisional Patent Application Ser. No. 60/110,407 filed Dec. 1, 1998, expired, each of which is hereby incorporated by reference in its entirety.

TECHNICAL FIELD OF THE INVENTION

The invention relates generally to a medical device, and more particularly, to a radiopaque implantable collagenous biomaterial device.

BACKGROUND OF THE INVENTION

It has become common to treat a variety of medical conditions by introducing an implantable medical device into the alimentary, circulatory, coronary, urological, renal, and other organ systems. For example, coronary stents can be inserted into coronary vessels via delivery catheters, such as balloon catheters. The ease of this delivery is facilitated in that the tips of the delivery catheters are often radiopaque, which provides visualization during standard radiographic inquiry.

In the case of aneurysm treatment, an aneurysm is caused by a weakening of the vessel wall, which causes an invagination of the vessel wall. Blood flow is inhibited at the neck of the aneurysm due to turbulence caused by blood entering and exiting the lumen of the aneurysm. Current medical treatment of aneurysms include the use of metal coils, such as the FDA approved Gugliemi Detachable Coil, inserted into the lumen of the aneurysm. However, this platinum coil is relatively soft and does not provide a complete packing of the aneurysm lumen. It is not uncommon for the aneurysm to re-canalize, enlarge, and even rupture. The heavy metal used in the coils provide the necessary radiographic visualization to ensure that the coils are localized properly and whether, during a subsequent examination, the coils remain in the situs.

However, there are problems associated with using synthetic materials, which include thrombus formation, immune response leading to rejection, and undesired occlusion of the vessel. Therefore, a better material for implantation in any application, such as coronary, vascular, body wall repair, orthopaedic, tissue graft, dermal, and other industries is needed. One such material is a newly discovered collagenous biomaterial, such as tissue submucosa.

Tissue implants in a purified form and derived from collagen-based materials have been manufactured and disclosed in the literature. Cohesive films of high tensile strength have been manufactured using collagen molecules or collagen-based materials. Aldehydes, however, have been generally utilized to cross-link the collagen molecules to produce films having high tensile strengths. With these types of materials, the aldehydes may leech out of the film, e.g. upon hydrolysis. Because such residues are cytotoxic, the films are poor tissue implants.

Other techniques have been developed to produce collagen-based tissue implants while avoiding the problems associated with aldehyde cross-linked collagen molecules. One such technique is illustrated in U.S. Pat. No. 5,141,747 wherein the collagen molecules are cross-linked or coupled at their lysine epsilon amino groups followed by denaturing the coupled, and preferably modified, collagen molecules. The disclosed use of such collagen material is for tympanic membrane repair. While such membranes are disclosed to exhibit good physical properties and to be sterilized by subsequent processing, they are not capable of remodeling or generating cell growth or, in general, of promoting regrowth and healing of damaged or diseased tissue structures.

In general, researchers in the surgical arts have been working for many years to develop new techniques and materials for use as implants to replace or repair damaged or diseased tissue structures, for example, blood vessels, aneurysms, muscle, ligaments, tendons and the like. It is not uncommon today, for instance, for an orthopedic surgeon to harvest a patellar tendon of autogenous or allogenous origin for use as a replacement for a torn cruciate ligament. The surgical methods for such techniques are known. Further, it has been common for surgeons to use implantable prostheses formed from plastic, metal and/or ceramic material for reconstruction or replacement of physiological structures. Yet, despite their wide use, surgical implanted prostheses present many attendant risks to the patient.

Researchers have also been attempting to develop satisfactory polymer or plastic materials to serve as functional tissue structures and/or other connective tissues, e.g., those involved in hernia and joint dislocation injuries. It has been discovered that it is difficult to provide a tough, durable plastic material which is suitable for long term connective tissue replacement. The tissues surrounding the plastic material can become infected and difficulties in treating such infections often lead to the failure of the implant or prostheses.

As mentioned above, various collagen-based materials have also been utilized for the above-mentioned tissue replacements; however, these materials either did not exhibit the requisite tensile strength or also had problems with infection and other immunogenic responses, encapsulation, or had other problems. In a related patent, U.S. Pat. No. 5,372,821, it is disclosed that a submucosa collagenous biomaterial may be sterilized by conventional techniques, e.g., aldehyde tanning, propylene oxide, gamma radiation and peracetic acid. No specific processing steps are disclosed except that the submucosa layer is first delaminated from the surrounding tissue prior to sterilization treatment.

Some materials considered desirable are biological materials (biomaterials) from autogenous, allogenous, or xenogeneic (heteroplastic) sources. Biomaterials are desirable as they can be malleable and less likely to be rejected as foreign. One such biomaterial is collagen. Collagen is a protein molecule that comes in many types. For example, collagen type I constitutes a significant amount of the collagen in the body. Type I is a heterotrimeric molecule, has a helical configuration, and is characterized by a Glycine-X-Y amino acid repeating sequence. Due to its abundance in the human body, collagen is being examined for its uses in medical treatment. One such treatment is for plugging vascular holes caused by the withdrawal of a catheter from the vessel. The collagen plug is inserted into the remaining hole as the hole begins to close up. In this manner, the collagen plug remains in the hole with the adjacent tissue holding it in place.

One of the problems encountered is that biomaterials presently used are not easy to radiographically visualize. Certain biological tissue, such as bone, visualize acceptably in radiography due to the density of the bone and the presence of biochemicals, such as calcium hydroxyapatite ($Ca_3PO_4$), or other calcium based minerals. However, in using other softer, less dense biomaterials, the difficulty in radiographic visualization increases. Thus, a softer biomaterial that is also radiographic is well-received.

SUMMARY OF THE INVENTION

The foregoing problems are solved and a technical advance is achieved in a newly discovered collagenous biomaterial and more particularly to a new biomaterial called submucosa. Submucosa, also known as tela submucosa, has been shown to be a remarkable biomaterial that promotes remodeling of the surrounding tissue, such as cellular invasion, host incorporation, and absorption of the submucosa material into the local tissue. Furthermore, submucosa has been shown to be acellular, strong, and exhibit a sidedness in that it has a differential porosity of its mucosal and serosal sides. Submucosa also does not trigger any viral response by the immune system as evidence suggests that it has no viral activity when checking for enveloped, non-enveloped, DNA, and RNA virus. Studies also show that submucosa increases the Th-2 immune response by increasing the production of interleukin-10 over interferon-γ, which indicates that the immune response is more accommodation than rejection. Due to these and other properties, submucosa makes for an excellent implantable biomaterial for use in multiple industries.

While collagenous biomaterials are known in the industries, none speak to the collagenous biomaterial being radiopaque as some biomaterials are radiolucent or the biomaterial is pure collagen, not the collagenous biomaterial described herein. Radiopacity can occur due to any of a number of conventional radiographic techniques, such as, but not limited to, the use of heavy metals, such as tantalum, barium, iodine, or bismuth. Furthermore, the use of such conventional materials facilitates easy manufacturing of the radiopaque implantable collagenous biomaterial. Radiopacity refers to a property whereby that conceived material easy at least slightly more opaque under Roentgenological visualizatian than the surrounding endogenous tissues.

In accordance with the present invention, provided is a collagenous implantable biomaterial, such as tela submucosa, wherein one type of tela submucosa includes small intestine submucosa (SIS) that is further advantageous in that it is radiopaque. Further provided in accordance with the present invention is the biocompatibility of the present device over other presently available biomaterials. The present invention further comprises a collagenous biomaterial that has an endotoxin level of less than 12 endotoxin units per gram. In some aspects of the present invention, the collagenous biomaterial is radiopaque and can take many shapes, such as, but not limited to, a coiled, helical, spring-like, randomized, branched, sheet-like, tubular, spherical, or fragmented shape. Furthermore, the present invention may take other shapes such as, but not limited to, fluidized, comminuted, liquefied, suspended, gel-like, injectable, powdered, ground, sheared, and solid shapes.

Advantageously, the present invention permits capitalization of the newly discovered collagenous biomaterial and its biotropic properties to be combined with radiopacity. This permits further industrial application of the disclosed medical device.

DETAILED DESCRIPTION OF THE INVENTION

In the discussions herein, a number of terms are used. In order to provide a clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

Biocompatibility—refers to the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary, integumentary, and genital tracts of animals.

Figure 1:
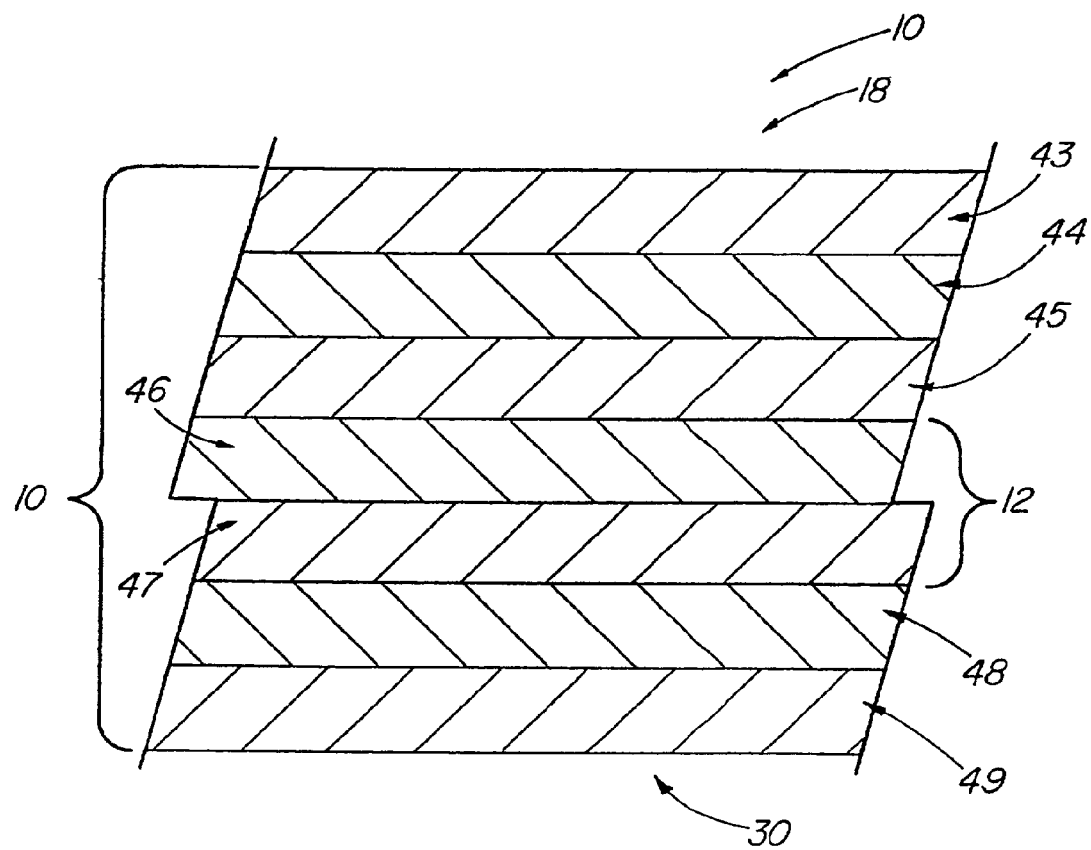
FIG. 1 represents the cross section of a small intestine.
Figure 2:
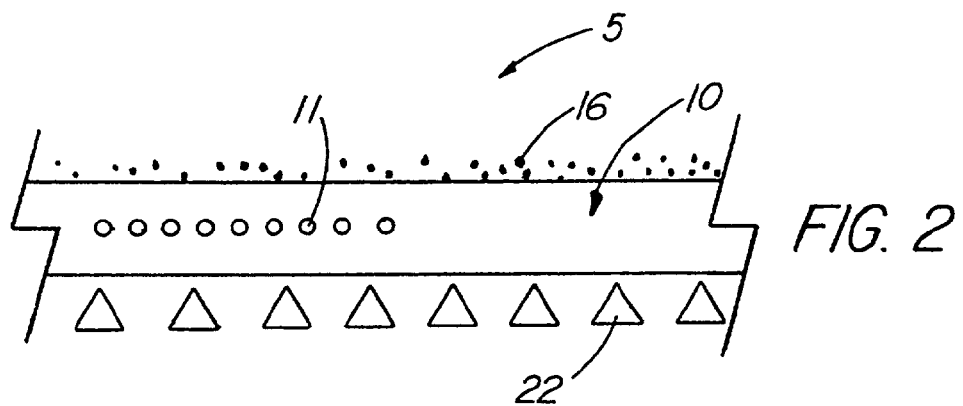
FIG. 2 represents the disposition of the radiopaque marker and the pharmacologic agent on the collagenous biomaterial.

With reference to FIGS. 1 and 2, the invention is generally directed to a radiopaque medical device 5, comprising a collagenous biomaterial 10 (also referred to as collagen-based matrices, tissue mucosa, tissue submucosa, intestines, biomaterial) that is radiopaque and is further described in the non-limiting disclosure set forth below.

Collagenous biomaterials discussed herein also include pericardium, basement membrane, amniotic membrane. Furthermore, one such collagenous biomaterial 10 includes a tissue submucosa, which further includes a small intestine submucosa 12, which is also described herein as one type of tela submucosa 12. Tela submucosa 12 is a multi-laminate structure, comprising the tunica submucosa, lamina muscularis mucosa, and the stratum compactum. However, the collagenous biomaterial herein includes the Intestinal Collagen Layer described in U.S. Pat. No. 5,733,337 to Carr and in 17 Nature Biotechnology 1083 (November 1999). Collagenous material 10 has biotropic agent 11 comprising at least one of a proteoglycan, glycosaminoglycan, glycoprotein, and growth factor. The tela submucosa 12 can be made using the techniques described in Cook et al., WIPO Publication WO 98/22158, dated 28 May 1998, which is the published application of PCT/US97/14855, the disclosure of which is set forth below. Other types of tela submucosa or tissue also include the following, the disclosures of which are hereby expressly incorporated by reference: Gastric Submucosa as described in WO 98/26291 (PCT/US97/22729), claiming priority to U.S. Provisional application 60/032,686; Liver tissue as described in WO 98/25637 (PCT/US97/22727), claiming priority to 60/032,680; Stomach Submucosa as described in WO 98/25636 (PCT/US97/23010), claiming priority to 60/032,683; and Urinary Bladder Submucosa as described in U.S. Pat. No. 5,554,389.

With reference to FIG. 1, shown is the collagenous biomaterial 10 comprising a multilayered device. The biomaterial 10 may have a serosal side 18 and a lumenal side 30. Where the collagenous biomaterial 10 is submucosa, the submucosa can be made by delaminating the mesenteric 43, tunica serosa 44, tunica muscularis 45 stratum compactum 48, and lamina propria 49 layers from the biomaterial 10. This leaves a multilayered device comprising at least the following layers: tunica submucosa 46, lamina muscularis mucosa 47. Accordingly, the tela submucosa layer can be further delaminated resulting in individual layers. Therefore, it is intended that the collagenous biomaterial 10 be an individual layer or a multilayered device.

As mentioned herein, the tela submucosa is rich in growth factors (GF), proteoglycans (PG), glycosaminoglycans (GAG), glycoproteins (GP), and other proteins. Accordingly, the collagenous biomaterial can comprise a pure collagen base material in which at least one of a GF, PG, GP, GAG, or other non-collagen proteins is disposed thereon. Such GF's include TGF alpha, TGF beta, PDGF, EGF, VEGF, FGF-2, KGF-7, KGF-10, Insulin-like GF, and Connective Tissue GF. Therefore, although the collagenous biomaterial 10 may be a pure collagen (such as synthetically derived collagen) with growth factors added later, the collagenous biomaterial 10 may also comprise pure collagen with PG's and/or GAG's later. Accordingly, it is preferable to use tela submucosa as it provides the host of beneficial agents.

One type of collagenous biomaterial 10, is tela submucosa 12, and as with many animal tissues, is generally aseptic in its natural state, provided the human or animal does not have an infection or disease. This is particularly the case since the tela submucosa 12 is an internal layer within the alimentary, integumentary, respiratory, urinary, and genital tracts of animals. Accordingly, it is generally not exposed to bacteria and other cellular debris such as the epithelium of the intestinal tract. One feature of the present invention is the discovery that by disinfecting the source tissue 10 for the tela submucosa 12 prior to delamination, the aseptic state of the tela submucosa 12 layer can be preserved or substantially preserved, particularly if the delamination process occurs under sterile conditions.

In particular, it has been discovered that disinfecting the tela submucosa 12 source, followed by removal of a purified biomaterial including the tela submucosa 12, e.g. by delaminating the tela submucosa 12 from the tunica muscularis and the tunica mucosa, minimizes the exposure of the tela submucosa 12 to bacteria and other contaminants. In turn, this enables minimizing exposure of the isolated tela submucosa 12 biomaterial to disinfectants or sterilants if desired, thus substantially preserving the inherent biochemistry of the tela submucosa 12 and many of the tela submucosa's beneficial effects.

A tela submucosa 12 implantable collagen biomaterial 10 according to the present invention 5 can, as indicated above, be obtained from the alimentary, respiratory, urinary, integumentary, or genital tracts of animals. Preferably, the tela submucosa 12 tissues, which are collagen-based and thus predominantly collagen, are derived from the alimentary tract of mammals, such as cows, sheep, dogs, and most preferably from the intestinal tract of pigs. A preferred source of whole small intestine 10 is harvested from mature adult pigs weighing greater than about 450 pounds. Intestines 10 harvested from healthy, non-diseased animals will contain blood vessels and blood supply within the intestinal 10 tract, as well as various microbes such as $E.\ coli$ contained within the lumen of the intestines 10. Therefore, disinfecting the whole intestine prior to delamination of the tela submucosa 12 substantially removes these contaminants and provides a preferred implantable tela submucosa 12 tissue which is substantially free of blood and blood components as well as any other microbial organisms, pyrogens or other pathogens that may be present. In effect, this procedure is believed to substantially preserve the inherent aseptic state of the tela submucosa 12, although it should be understood that it is not intended that the present invention be limited by any theory. All that is required or be met is that the biomaterial 10 satisfies the above-mentioned criteria.

It is also desirable that the collagenous biomaterial 10 according to the present invention 5 be substantially free of any antiviral agents or any antimicrobial type agents which can affect the biochemistry of the biomaterial and its efficacy upon implantation. In the past, one method of treating such tissue material is to rinse the delaminated tissue in saline and soak it in an antimicrobial agent, for example, as disclosed in U.S. Pat. No. 4,956,178. While such techniques can optionally be practiced with isolated collagenous mucosa 10 or submucosa 10 of the present invention, preferred processes according to the present invention avoid the use of antimicrobial agents and the like which can not only affect the biochemistry of the collagenous biomaterial 10 but also can be unnecessarily introduced into the tissues of the patient.

As discussed above, it has been discovered that a highly pure form of an implantable tela submucosa 12 collagen biomaterial can be obtained by first disinfecting a tela submucosa 12 source prior to removing a purified collagen biomaterial including the tela submucosa 12 layer, e.g. by delaminating the tela submucosa 12 source. It has also been discovered that certain processing advantages as well as improved properties of the resultant tela submucosa 12 layer are obtained by this process, including greater ease in removing attached tissues from the submucosa layer, and a characteristic, low contaminant profile.

Processes of the invention desirably involve first rinsing the tela submucosa 12 source one or more times with a solvent, suitably water. The rinsing step is followed by treatment with a disinfecting agent. The disinfecting agent is desirably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa matrices as described herein, preferably exhibiting a bioburden of essentially zero and/or essential freedom from pyrogens. In this regard, desirable processes of the invention involve immersing the tissue source 10 (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

A preferred peroxy disinfecting agent is hydrogen peroxide. The concentration of hydrogen peroxide can range from about 0.05% to 30% by volume. More preferably the hydrogen peroxide concentration is from about 1% to 10% by volume and most preferably from about 2% to 5% by volume. The solution can or can not be buffered to a pH from about 5 to 9. More preferably the pH is from about 6 to 7.5. These concentrations can be diluted in water or in an aqueous solution of about 2% to about 30% by volume alcohol. Most preferably the alcohol is ethanol. The solution temperature can range from about 15 to 50° C. More preferably the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes.

A preferred organic peroxide disinfecting agent is perpropionic acid. The concentration of perpropionic acid can range from about 0.1% to 10% by volume. More preferably the perpropionic acid concentration is from about 0.1% to 1.0% by volume and most preferably from about 0.2% to 0.5% by volume. These concentrations of perpropionic acid can be diluted in water or in an aqueous solution of about 2% to about 30% by volume alcohol. Most preferably the alcohol is ethanol. The tela submucosa 12 tissue source can be exposed to the organic peroxide solution for periods from about 15 minutes to about 40 hours, and more typically in the range of about 0.5 hours to about 8 hours. Other peroxy disinfecting agents are suitable for use as described in "Peroxygen Compounds", S. Block, in *Disinfection, Sterilization and Preservation*, S. Block, Editor, 4th Edition, Philadelphia, Lea & Febiger, pp. 167-181, 1991; and "Disinfection with peroxygens", M. G. C. Baldry and J. A. L. Fraser, in *Industrial Biocides*, K. Payne, Editor, New York, John Wiley and Sons, pp. 91-116, 1988.

Another oxidizing disinfecting agent is chlorhexidine (1,6-di(4-chlorophenyldiguanido)hexane) in its digluconate form. The concentration of chlorhexidine digluconate can range from about 0.1% to 15% by weight. More preferably, the chlorhexidine digluconate concentration is from about 0.1% to 2% by weight and most preferably from about 0.2% to 5% by weight. The solution can or can not be buffered to a pH from about 5 to 8. More preferably the pH is from about 5.5 to 7. These concentrations can be diluted in water or in an aqueous solution of about 2% to about 20% by volume alcohol. Most preferably the alcohol is ethanol at a concentration of about 5% to 10%. The solution temperature can range from about 15 to 30° C. The exposure time can range from about 10 to 400 minutes. More preferably the exposure time is from about 30 to 60 minutes. Other chlorine agents are described in "Chlorhexidine", G. W. Denton, in *Disinfection, Sterilization and Preservation*, S. Block, Editor, 4th Edition, Philadelphia, Lea & Febiger, pp. 274-289, 1991.

In preferred preparative processes, a peracid or other disinfecting agent can be dissolved in a dilute aqueous alcohol solution, preferably wherein the alcohol has from 1 to about 6 carbon atoms, and wherein the alcohol can generally comprise from about 1% to about 30% by volume of the solution. More preferred alcohols for use in the invention are selected from the group consisting of ethanol, propanols and butanols. Ethanol is a preferred alcohol for these purposes.

When a peracid is used in the disinfection, it is preferably selected from the group consisting of peracetic acid, perpropionic acid or perbenzoic acid. Peracetic acid is the most preferred disinfecting agent. The peracetic acid is preferably diluted into about a 2% to about 10% by volume alcohol solution. The concentration of the peracetic acid can range, for example, from about 0.05% by volume to about 1.0% by volume. Most preferably the concentration of the peracetic acid is from about 0.1% to about 0.3% by volume. Hydrogen peroxide can also be used as a disinfecting agent. Alternatively, or in addition, the tela submucosa 12 tissue source, e.g. from small intestine 12, can be disinfected utilizing disinfecting agents such as glutaraldehyde, formalin and the like, which are also known for their ability to introduce substantial crosslinking into collagen matrices 10, in contrast to the action of other disinfecting agents such as peracids which can be used to disinfect without introducing such crosslinking. Additionally, the tela submucosa 12 source can be treated with radiation, e.g., gamma radiation, for purposes of disinfection.

Variations on the disinfection process can also include the following:
1. Intestine is treated with 0.2% peracetic acid, 5% ethanol solution at a ratio of 10:1 solution to intestine ratio by weight. Solution has a pH of 2.6. Solution and intestine are vigorously mixed for two hours.
2. Intestine is treated with 1% peracetic acid, 25% ethanol solution at a ration of 5:1 solution to intestine ratio by weight. Solution has a pH of 2. Solution and intestine are vigorously mixed for one hour.
3. Intestine is treated with 1% peracetic acid, 15% ethanol, and 10% hydrogen peroxide solution at a ratio of 5:1 solution to intestine ratio by weight. Solution and intestine are vigorously mixed for one hour.
4. Whole small intestine is rinsed four times with high purity water for 15 minutes. The intestine is then subjected to 2.5 MRAD Electron Beam radiation.
5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa 12 layer is delaminated from its source 10, e.g., whole intestine, cow uterus and the like. It has been found that by following this post-disinfection-stripping procedure, it is easier to separate the tela submucosa 12 layer from the attached tissues, e.g. at least from attached tunica muscularis tissue, as compared to stripping the tela submucosa 12 layer prior to disinfection. Moreover it has been discovered that the resultant tela submucosa 12 layer in its most preferred form exhibits superior histology, in that there is less attached tissue and debris on the surface compared to a tela submucosa 12 layer obtained by first delaminating the tela submucosa 12 layer from its source and then disinfecting the layer. Moreover, a more uniform tela submucosa 12 tissue can be obtained from this process, and a tela submucosa 12 having the same or similar physical and biochemical properties can be obtained more consistently from each separate processing run. Importantly, a highly purified, substantially sterile tela submucosa 12 is obtained by this process. The stripping of the tela submucosa 12 source is preferably carried out by utilizing a disinfected or sterile casing machine, to produce a tela submucosa 12 which is substantially sterile and which has been minimally processed. A suitable casing machine is the Model 3-U-400 Stridhs Universal Machine for Hog Casing, commercially available from the AB Stridhs Maskiner, Götoborg, Sweden. Therefore, the measured bioburden levels are minimal or substantially zero. Of course, other means for delaminating the tela submucosa 12 source can be employed without departing from the present invention, including for example those means well known in the art, including delaminating by hand.

It has also been discovered that more preferred processes according to the present invention, not only will eliminate or significantly reduce contaminants contained in the tela submucosa 12 collagen biomaterial 10, but also will produce a tissue which exhibits no substantial degradation of physical and mechanical properties, e.g., differential porosity (i.e. wherein one side of the submucosa layer has greater porosity than the other side), and good strength, for example burst strength. Also, it has been discovered that more preferred processes do not affect the differential porosity of the tela submucosa 12 collagen biomaterial 10, which ultimately affects the level of efficacy of this tissue implant. For example, the tissue is not necessarily treated with a crosslinking agent or a material that disrupts the porosity or inherent, native structure of the collagen biomaterial. Moreover, when hydrogen peroxide is employed, the biomaterial as a whole has greater porosity as well as a higher oxygen content. This helps to ensure the absence of contaminants e.g., endotoxins, pyrogens, and the like.

Preferred collagen-based matrices 10 of the invention, preferably submucosa-containing matrices 12, are also characterized by the low contaminant levels set forth in Table 1 below, each contaminant level taken individually or in any combination with some or all of the other disclosed contaminant levels. The abbreviations in Table 1 are as follows: CFU/g=colony forming units per gram; PFU/g=plaque forming units per gram; µg/mg=micrograms per milligram; ppm/kg=parts per million per kilogram; and EU/g=endotoxin units per gram.

TABLE 1

| FEATURE | FIRST PREFERRED LEVEL | SECOND PREFERRED LEVEL | THIRD PREFERRED LEVEL |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESSING AGENT | <100,000 ppm/kg | <1,000 ppm/kg | <100 ppm/kg |

Even more preferred collagen-based matrices 10 of the invention contain an endotoxin level of less than 1 EU/g, and most preferably less than 0.5 EU/g.

Purified collagen-based matrices 10 according to the present invention can be processed in a number of ways, to provide collagenous matrices 10 useful both in vitro and in vivo. For example, the submucosa can be configured to provide tissue grafts useful in vascular applications, e.g. as generally described in U.S. Pat. Nos. 2,127,903 and 4,902,508.

The tela submucosa 12 of the invention possesses mechanical properties highly desirable for tissue graft materials in vascular applications, including low porosity index, high compliance, and a high burst strength. One skilled in the art will appreciate that the preferred tissue graft material will be of low enough porosity to prevent intraoperative hemorrhage and yet of high enough porosity to allow extension of a newly-developed vasa vasorum through the graft material to nourish the neointimal and luminal surface.

Tela submucosa 12 tissue of the present invention 5 can also be processed to provide fluidized compositions, for instance using techniques as described in U.S. Pat. No. 5,275,826. In this regard, solutions or suspensions of the tela submucosa 12 can be prepared by comminuting and/or digesting the tela submucosa 12 with a protease (e.g. trypsin or pepsin), for a period of time sufficient to solubilize the tissue and form substantially homogeneous solution. The submucosa starting material is desirably comminuted by tearing, cutting, grinding, shearing or the like. Grinding the submucosa in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted tela submucosa 12 can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25EC. The higher viscosity graft compositions can have a gel or paste consistency.

Fluidized 13 tela submucosa 12 of this invention finds use as an injectable heterograft 13 for tissues, for example, bone or soft tissues, in need of repair or augmentation most typically to correct trauma or disease-induced tissue defects. The present fluidized submucosa compositions are also used advantageously as a filler for implant constructs comprising, for example, one or more sheets of tela submucosa 12 formed into sealed (sutured) pouches for use in cosmetic or trauma-treating surgical procedures.

In one illustrative preparation, tela submucosa 12 prepared as described herein is reduced to small pieces (e.g. by cutting) which are charged to a flat bottom stainless steel container. Liquid nitrogen is introduced into the container to freeze the specimens, which are then comminuted while in the frozen state to form a coarse tela submucosa 12 powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the tela submucosa 12 specimens to keep them frozen.

Other methods for comminuting tela submucosa 12 specimens can be utilized to produce a tela submucosa 12 powder usable in accordance with the present invention 5. For example, tela submucosa 12 specimens can be freeze-dried and then ground using a manual arbor press or other grinding means. Alternatively, tela submucosa 12 can be processed in a high shear blender to produce, upon dewatering and drying, a tela submucosa 12 powder.

Further grinding of the tela submucosa 12 powder using a prechilled mortar and pestle can be used to produce a consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, a tela submucosa 12 powder can be sifted through a wire mesh, collected, and subjected to proteolytic digestion to form a substantially homogeneous solution. For example, the powder can be digested with 1 mg/ml of pepsin (Sigma Chemical Co., St. Louis Mo.) and 0.1 M acetic acid, adjusted to pH 2.5 with HCl, over a 48 hour period at room temperature. After this treatment, the reaction medium can be neutralized with sodium hydroxide to inactivate the peptic activity. The solubilized submucosa 12 can then be concentrated by salt precipitation of the solution and separated for further purification and/or freeze drying to form a protease-solubilized intestinal submucosa 12 in powder shape.

Fluidized tela submucosa 12 compositions of this invention find wide application in tissue replacement, augmentation, and/or repair. The fluidized submucosal compositions can be used to induce regrowth of natural connective tissue or bone in an area of an existent defect. By injecting an effective amount of a fluidized submucosa composition into the locale of a tissue defect or a wound in need of healing, one can readily take advantage of the biotropic properties of the tela submucosa 12. Interestingly, fluidizing SIS 12 by comminution or enzymatic degradation does not result in any appreciable loss of biotropic activities, as shown in U.S. Pat. No. 5,275,826.

It is also possible to shape large surface area constructs by combining two or more tela submucosa 12 segments of the invention 5, for instance using techniques as described in U.S. Pat. No. 2,127,903 and/or International Publication No. WO 96/32146, dated 17 Oct. 1996, publishing International Application No. PCT/US96/04271, filed 5 Apr. 1996. Thus, a plurality of tela submucosa 12 strips can be fused to one another, for example by compressing overlapping areas of the strips under dehydrating conditions, to form an overall planar construct having a surface area greater than that of any one planar surface of the individual strips used to shape the construct. Shapes can be made by using sutures, staples, biocompatible adhesives such as collagen binding pastes, or dehydrating overlapping structures then heating the structure as described in U.S. Pat. No. 3,562,820.

As described herein, the invention can take many shapes 13, such as coiled, helical, spring-like, randomized, branched, sheet-like, tubular, spherical, fragmented, fluidized, comminuted, liquefied, suspended, gel-like, injectable, powdered, ground, sheared, and solid material shape.

The tela submucosa 12 powder can be used alone, or in combination with one or more additional bioactive agents such as physiologically compatible minerals, growth factors, antibiotics, chemotherapeutic agents, antigen, antibodies, enzymes and hormones. Preferably, the powder-form implant will be compressed into a predetermined, three-dimensional shape, which will be implanted into the bone region and will substantially retain its shape during replacement of the graft with endogenous tissues.

Tela submucosa 12 of the invention can also be used as a cell growth substrate, illustratively in sheet, paste or gel shape in combination with nutrients which support the growth of the subject cells, e.g. eukaryotic cells such as endothelial, fibroblastic, fetal skin, osteosarcoma, and adenocarcinoma cells (see, e.g. International Publication No. WO 96/24661 dated 15 Aug. 1996, publishing International Application No. PCT/US96/01842 filed 9 Feb. 1996. In preferred forms, the tela submucosa 12 substrate composition will support the proliferation and/or differentiation of mammalian cells, including human cells.

The inventive tela submucosa 12 can also serve as a collagenous biomaterial in compositions for producing transformed cells, (see, e.g., International Publication No. WO 96/25179 dated 22 Aug. 1996, publishing International Application No. PCT/US96/02136 filed 16 Feb. 1996; and International Publication No. WO 95/22611 dated 24 Aug. 1995, publishing International Application No. PCT/US95/02251 filed 21 Feb. 1995). Such compositions for cell transformation will generally include purified tela submucosa 12 of the present invention, for example in fluidized or paste shape as described in U.S. Pat. No. 5,275,826, in combination with a recombinant vector (e.g. a plasmid) containing a nucleic acid sequence with which in vitro or in vivo target cells are to be genetically transformed. The cells targeted for transformation can include, for example, bone progenitor cells.

In order to promote a further understanding of the present invention and its features and advantages, the following specific Examples are provided. It will be understood that these specific Examples are illustrative, and not limiting, of the present invention.

EXAMPLE 1

Thirty feet of whole intestine from a mature adult hog is rinsed with water. This material is then treated in a 0.2% by volume peracetic acid in a 5% by volume aqueous ethanol solution for a period of two hours with agitation. The tela submucosa 12 layer is then delaminated in a disinfected casing machine from the whole intestine. The delaminated tela submucosa 12 is rinsed four (4) times with sterile water and tested for impurities or contaminants such as endotoxins, microbial organisms, and pyrogens. The resultant tissue was found to have essentially zero bioburden level. The tela submucosa 12 layer separated easily and consistently from the whole intestine and was found to have minimal tissue debris on its surface.

EXAMPLE 2

A ten foot section of porcine whole intestine is washed with water. After rinsing, this section of tela submucosa 12 intestinal collagen source material is treated for about two and a half hours in 0.2% peracetic acid by volume in a 5% by volume aqueous ethanol solution with agitation. Following the treatment with peracetic acid, the tela submucosa 12 layer is delaminated from the whole intestine. The resultant tela submucosa 12 is then rinsed four (4) times with sterile water. The bioburden was found to be essentially zero.

EXAMPLE 3

A small section of the tela submucosa 12 intestinal collagen material was subcutaneously implanted in a rat. Within 72 hours, significant angiogenesis was observed.

EXAMPLE 4

Two sections of small intestine are processed by differing methods. The first section is rinsed in tap water, disinfected for 2 hours in a 5% by volume aqueous ethanol solution comprising 0.2% by volume peracetic acid, pH approximately 2.6, delaminated to the tela submucosa 12, rinsed in purified water, divided into two samples and rapidly frozen.

The second section is rinsed in tap water, delaminated to the tela submucosa 12, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

EXAMPLE 5

Three sections of small intestine are processed by differing methods. The first is rinsed in tap water, disinfected for 2 hours in a 5% by volume aqueous ethanol solution comprising 0.2% by volume peracetic acid, pH about 2.6, delaminated to the tela submucosa 12, rinsed in purified water, and rapidly frozen. The second is rinsed in tap water, delaminated to the tela submucosa 12, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. The third is rinsed in tap water, delaminated to the tela submucosa 12, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

EXAMPLE 6

Two sections of porcine small intestine were infected with $7 \times 10^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

EXAMPLE 7

Purified tela submucosa 12, prepared as described herein, was tested to determine its nucleic acid content. Four samples of material weighing 5 mg each were subjected to DNA/RNA extraction as detailed in the DNA/RNA Isolation Kit by Amersham Lifescience Inc., Arlington Heights, Ill. Nucleic acid quantitation was performed by spectrophotometric determination of solution optical densities at 260 nm and 280 nm. The average nucleic acid content was 1.9±0.2 mg per milligram of material.

Small intestinal submucosa, prepared as described by U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4±0.2 mg per milligram of material.

EXAMPLE 8

Sections of tela submucosa 12 prepared according to the methods described herein were sent to an independent testing laboratory (NamSA, Inc., Northwood, Ohio) for biocompatibility testing as described in the standard ISO 10993, and FDA guidelines for endotoxins. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

EXAMPLE 9

Using the procedure set forth in U.S. Pat. No. 5,460,962, two samples were analyzed. The first Kemp sample indicated an endotoxin level greater than 24 endotoxin units per gram and the second Kemp sample indicated an endotoxin level greater than 28 endotoxin units per gram. Thus, when using the procedure set forth in Kemp '962, the endotoxin levels fall outside the biocompatibility levels as set forth in FDA guidelines for an implantable medical device.

EXAMPLE 10

Using the procedures set forth in U.S. Pat. Nos. 4,902,508 and 5,372,821 issued to Badylak, the endotoxin level shown ranges as high as 23.9 endotoxin units per gram per sample. This falls outside the permissible range and thus does not the meet the criteria of biocompatibility. The invention, prepared in the above prescribed manner of disinfection first then delamination, was observed to have an endotoxin level of less than 12 endotoxin units per gram, and more particularly, reported an endotoxin level of less than 5 endotoxin units per gram. Thus, the material of the present invention is biocompatible as defined above.

Figure 3:
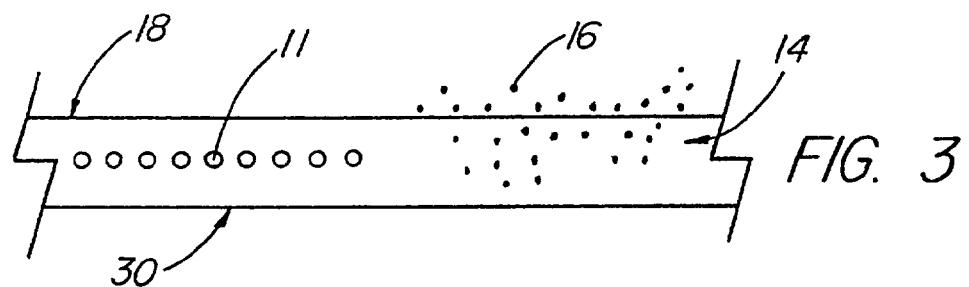
FIG. 3 represents the disposition of the radiopaque marker in another embodiment.

With reference to FIGS. 2 and 3, the collagen biomaterial 10 can be made radiopaque by a variety of conventional procedures, none of which has yet been applied to tela submucosa 12. In one embodiment of the invention 5, the collagen material 10 has a shape 13, namely made into sheets, either in lyophilized or non-lyophilized form. Any radiopaque substance 16, including but not limited to, tantalum such as tantalum powder, can be spread along the surface of the tela submucosa 12, such as on the serosal side 18. Other radiopaque materials 16 comprise bismuth and barium, including but not limited to, bismuth oxychloride and barium sulphate, as well as other conventional markers 16, such as iodine. As used herein, the term "disposed" on shall be construed to include disposed on, disposed throughout, disposed in, disposed with, disposed along with, applied on, applied with, applied through, applied in, applied in conjunction with, and the like. With particular reference to tela submucosa 12, the differential porosity of the material can enable more radiopaque material 16 to be disposed on the tela submucosa 12.

In one particular embodiment, radiopaque marker tantalum powder 16 was disposed on a sheet of tela submucosa 12 by rubbing it onto the serosal side 18 of the tela submucosa 12. The tela submucosa 12 was then made into various shapes 13, such as, but not limited to, having the shape 13 of a brush-like, braided, branched, helical, spherical, cubic, cylindrical, tubular, injectable, randomized, layered, and sheet-like shapes. For example, an injectable shape 13 of the invention can be readily made by comminuting the invention 5 into small fibrils, fragments, or the like, then suspending them in solution, such as, but not limited to, a biocompatible gelatin suspension. Due to the viscosity of the gelatin suspension, the invention 5, when injected into the lumen of an aneurysm, will stay in the lumen and provide the therapeutic benefit to the aneurysm.

Figure 4:
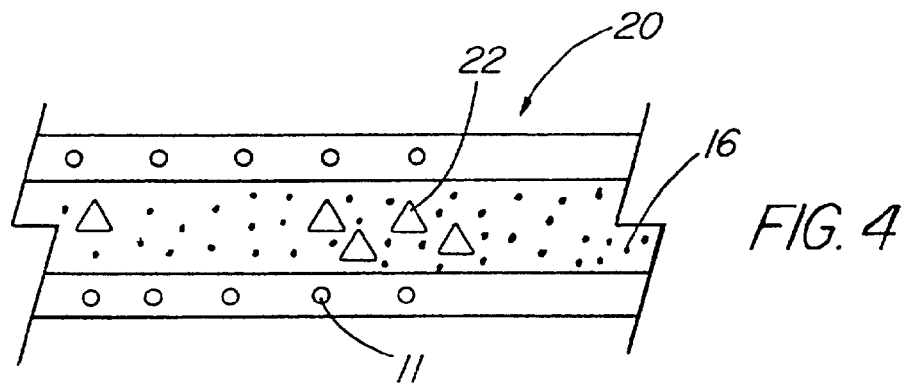
FIG. 4 represents the plurality of layers of another embodiment of the invention.

With reference to FIG. 4, the invention 5 and collagenous biomaterial 10 can be made in layers 20. In this manner, the collagenous material 10 can increase its structural integrity, strength, and applicability. In one embodiment of the invention 5, a dual layer 20 of collagenous biomaterial 10 can be used in sheets 13 and disposed in between the layers 20 is the either the radiomarker 16 or pharmacologic agent 22, or both.

Figure 5:
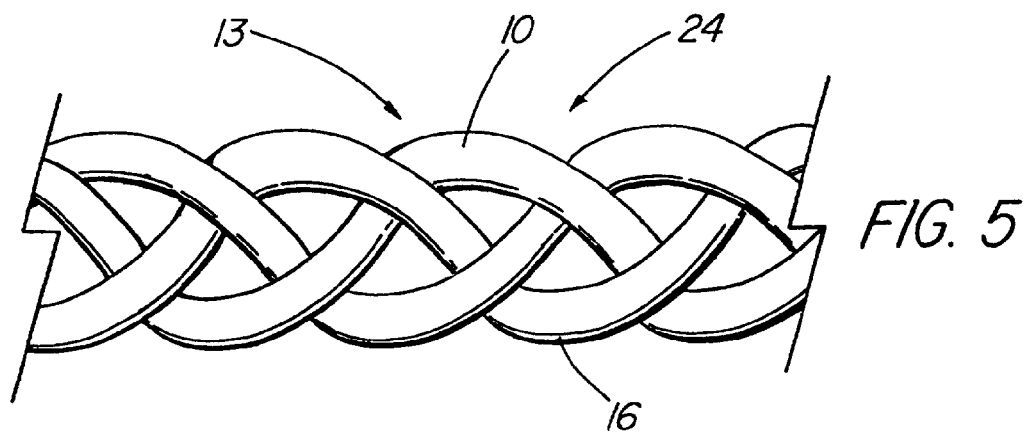
FIG. 5 represents a braid shape of an embodiment of the invention.
Figure 6:
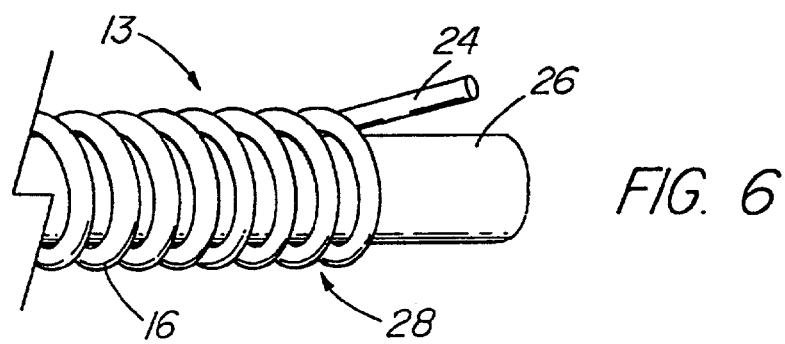
FIG. 6 represents the coil shape of an embodiment of the invention.

The collagenous biomaterial 10 of the present invention 5 can be in lyophilized or non-lyophilized form. Where the biomaterial 10 is lyophilized, the biomaterial 10 has a shape memory characteristic in that the shape of the material after lyophilization or after air drying, will be reformed once the material is rehydrated. For example, one embodiment of the present invention 5 includes the coil shape 13. Strips 13 of the biomaterial 10 can be shaped into a braid 24, as seen in the exemplary FIG. 5, to increase its strength or size. Since a braid comprises many constituent threads, the radiopaque marker 16 may be disposed on the collagenous material 10 threads, or marker 16 may be radiopaque thread itself. For example, the barium could be made into a thread or may be combined with other material to form a barium compound thread as a derivative of barium. The coil shape 28, though, is not limited to a multiple strip braid 24, as coil 28 can be formed with one strip. The braided material 24 can then be wound around a mandrel 26, as seen in the exemplary FIG. 6, to form a coil 28. The coil shape 28 is then lyophilized by freezing the coil 28 and dehydrating the coil 28 under vacuum pressure. The coil 28 then retains shape memory. The coil 28 then can be re-hydrated in a solution to become malleable again and will retain its shape memory. For example, after the coils 28 are made and dehydrated, the coil 28 can then be unwound or crumpled up to facilitate delivery to the situs via a delivery catheter. When the coil 28 comes in contact with the body fluids, it will re-hydrate and reform into a coil 28. In this manner, delivery of coils 28 to an aneurysm lumen is greatly facilitated. Furthermore, when used as an embolization device 5, the device 5 can be readily inserted proximal to the targeted occlusion area and will reform into the desired shape at the desired occlusion situs.

Alternatively the materials can be dried without the freezing step. This drying can be done under purified air flow or under vacuum pressure. The coils characteristics change such that the re hydration time decreases. In similar fashion, the pharmacologic agent 22 can be disposed on the collagenous material 10. As used herein, the pharmacologic agent 22 includes, but is not limited to, growth factors, proteins, proteoglycans, glycosaminoglycans, physiological compatible minerals, antibiotics, chemotherapeutic agents, enzymes, drugs, genetic material, and hormones. The agent 22 can be disposed on the serosal 18 or mucosal 30 sides of the submucosa, or can be disposed on the same or opposite sides of the collagenous material 10. Consideration of placement can be important depending on the desired shape of the final device. For example, where the shape 13 is tubular, it can be desirable to place the pharmacologic agent 22 on the abluminal 18 surface since that surface will be in contact with the surrounding tissue. On the other hand, if systemic release of the agent 22 is contemplated, then the agent 22 can be placed on the lumenal 30 side to permit the blood to contact the agent 22 and carry it away. Utilizing the braid shape 24, each individual strip can be treated with different agents 22.

It will be appreciated that variations of the above-described processing procedures are intended to be within the scope of this invention. For example, the source tissue for the collagenous biomaterial, e.g., stomach, whole intestine, cow uterus and the like, can be partially delaminated, treated with a disinfecting or sterilizing agent followed by complete delamination of the tela submucosa 12. Illustratively, attached mesentery layers, and/or serosa layers of whole intestine can be advantageously removed prior to treatment with the disinfecting agent, followed by delamination of remaining attached tissues from the tela submucosa 12. These steps can or can not be followed by additional disinfection steps, e.g., enzymatic purification and/or nucleic acid removal. Alternatively, the tela submucosa 12 source can be minimally treated with a disinfecting or other such agent, the tela submucosa 12 delaminated from the tunica muscularis and tunica mucosa, followed by a complete disinfection treatment to attain the desired contaminant level(s). All such variations and modifications are contemplated to be a part of the process described herein and to be within the scope of the invention. Many alterations and modifications can be made by those of ordinary skill in the art without departing from the spirit and scope of the invention. The illustrated embodiments have been shown only for purposes of clarity and examples, and should not be taken as limiting the invention as defined by the appended claims, which include all equivalents, whether now, or later devised.

What is claimed is:

1. A method for treating an aneurysm in a patient, comprising:

providing a coil implant comprising a collagenous implantable biomaterial, wherein the collagenous implantable biomaterial comprises a plurality of constituent threads comprising tela submucosa of a warm-blooded vertebrate tissue source, said constituent threads shaped into a braid and forming an elongated braided collagenous biomaterial, wherein the braided collagenous biomaterial is wound and then lyophilized while wound to form a coil having a plurality of turns and having shape memory for the shape of the coil, said shape memory allowing the braided collagenous biomaterial to be unwound to an unwound state and said shape memory causing the braided collagenous biomaterial to reform from the unwound state into the coil when rehydrated, wherein a radiopaque marker is disposed on the constituent threads, and wherein said collagenous biomaterial is effective upon implantation to promote cellular invasion and ingrowth;

delivering the coil implant in said unwound state through a catheter to a lumen of the aneurysm; and radiographically visualizing said radiopaque marker.

2. The method of claim 1, wherein said radiopaque marker comprises tantalum, bismuth, or barium.

3. The method of claim 1, wherein said radiopaque marker includes tantalum.

4. The method of claim 1, wherein said collagenous implantable biomaterial retains at least one biotropic agent from said warm-blooded vertebrate tissue source, wherein said biotropic agent is a proteoglycan, glycosaminoglycan, glycoprotein or a growth factor.

5. The method of claim 4, wherein said collagenous implantable biomaterial retains a growth factor from said warm-blooded vertebrate tissue source.

6. The method of claim 1, wherein said radiopaque marker includes tantalum.

7. A method for treating an aneurysm in a patient, comprising:

providing a coil implant comprising a collagenous implantable biomaterial comprising a plurality of constituent threads comprising tela submucosa from a warm-blooded vertebrate tissue source, said constituent threads shaped into a braid and forming an elongated braided collagenous biomaterial, wherein the braided collagenous biomaterial is wound and then lyophilized while wound to form a lyophilized coil having a plurality of turns and having shape memory for the shape of the coil, said shape memory allowing the braided collagenous biomaterial to be unwound to an unwound state and said shape memory causing the braided collagenous biomaterial to reform from the unwound state into the coil when rehydrated, wherein at least one constituent thread is a radiopaque thread, and said collagen implantable biomaterial being effective upon implantation to promote cellular invasion and ingrowth to occlude the site;

delivering the coil implant in said unwound state through a catheter to a lumen of the aneurysm; and radiographically visualizing said radiopaque marker.

8. The method of claim 7, wherein said radiopaque marker comprises tantalum, bismuth, or barium.

9. The method of claim 7, wherein said radiopaque marker includes tantalum.

10. The method of claim 7, wherein said collagenous implantable biomaterial retains at least one biotropic agent from said warm-blooded vertebrate tissue source, wherein said biotropic agent is a proteoglycan, glycosaminoglycan, glycoprotein or a growth factor.

11. The method of claim 7, wherein said collagenous implantable biomaterial retains a growth factor from said warm-blooded vertebrate tissue source.

* * * * *